United States Patent
Kwak

[19]

[11] Patent Number: 6,106,285
[45] Date of Patent: Aug. 22, 2000

[54] APPARATUS FOR TRACING CENTRIC RELATION OF MANDIBLE

[76] Inventor: Heung Ku Kwak, Mokdong APT. 921-201, 312, Shinjeong-dong, Yangchon-ku, Seoul, Rep. of Korea

[21] Appl. No.: 09/290,137

[22] Filed: Apr. 13, 1999

[30] Foreign Application Priority Data

Apr. 16, 1998 [KR] Rep. of Korea ......................... 98-6002

[51] Int. Cl.[7] .................................................. A61C 19/04
[52] U.S. Cl. .............................................. 433/68; 433/75
[58] Field of Search .................................. 433/68, 69, 72, 433/75; 33/513

[56] References Cited

U.S. PATENT DOCUMENTS

| | | |
|---|---|---|
| 1,776,474 | 9/1930 | Messerman .............................. 433/68 |
| 2,389,063 | 11/1945 | Lang ........................................ 433/69 |
| 2,481,203 | 9/1949 | Davies et al. ............................. 433/69 |
| 3,431,649 | 3/1969 | Guichet .................................... 433/69 |
| 3,482,312 | 12/1969 | Smith ....................................... 433/69 |
| 4,055,896 | 11/1977 | Corbett ..................................... 433/69 |
| 5,186,624 | 2/1993 | Gottsleben ................................ 433/69 |
| 5,188,529 | 2/1993 | Luth ......................................... 433/68 |

*Primary Examiner*—John J. Wilson
*Attorney, Agent, or Firm*—Ladas & Parry

[57] ABSTRACT

Disclosed is an apparatus for tracing a centric relation of a mandible including a stylus arranged at a point, where an occlusal plane and a mid-sagittal plane cross a line extending between central fossae of mandibular first molars, and a tracing-plate adapted to be mounted to a maxilla at a region corresponding to the stylus. The tracing apparatus also includes a ball threadedly coupled to the stylus in such a fashion that it is fitted around the stylus in the form of a nut and cylinder, a base plate having a circular hole provided with an arc-shaped surface serving as a seat for the ball, a support plate arranged over the base plate and coupled to the base plate while being vertically spaced from the base plate, the support plate having a circular hole provided with an arc-shaped surface cooperating with the arc-shaped surface of the base plate to clamp the ball therebetween when the support plate is in a state coupled to the base plate, and a plurality of support members each mounted to a desired portion of the base plate at one end thereof and engaged with a desired surface portion of a dentition at the other end thereof, thereby maintaining the base plate at a desired position. Since the ball is selectively pivotable, it is possible to easily and conveniently adjust the position and orientation of the stylus.

6 Claims, 12 Drawing Sheets

Individual tray

APPARATUS FOR TRACING CENTRIC RELATION OF MANDIBLE

BACKGROUND OF THE INVENTION

1. Field of the Invention

The present invention relates to an apparatus for tracing a centric relation of a mandible, and more particularly to a tracing apparatus in which a stylus used to check a centric relation of a mandible in the formation of prosthesis or artificial dentures is coupled to a nut-shaped ball supported by a base plate mounted to a dentition and a support plate threadedly coupled to the base plate in such a fashion that it can be selectively pivotable, thereby eliminating use of any separate dentition supporting wires.

2. Description of the Prior Art

Generally, a positional relation of the mandible with respect to the maxilla at a certain mandibular position is called a "maxillary-mandibular jaw relation". In order to make an accurate diagnosis or remedy for dental patients, it is frequently necessary to trace such a maxillary-mandibular jaw relation. In such a case, a three-dimensional maxillary-mandibular jaw relation, that is, longitudinal, lateral, and vertical maxillary-mandibular jaw relations, should be accurately traced. The reference point of a maxillary-mandibular jaw relation is simply called a "centric relation". This centric relation is a horizontal maxillary-mandibular jaw relation regularly and repeatedly traced in accordance with a patient's vertical dimension. Such a centric relation is a relaxed positional relation of the neuro-muscular system. There are various methods for tracing such a centric relation. One method is to instruct a patient to conduct longitudinal and lateral mandibular movements by himself under the condition in which tracing devices are mounted to the maxilla and mandible in the oral cavity of the patient, and to record movement paths respectively defining the longitudinal and lateral mandibular movements on a horizontal plane. Such movement paths are called "Gothic arch tracings". An example of such Gothic arch tracings is illustrated in FIG. 1. Referring to FIG. 1, a mandibular movement is defined by a forward longitudinal mandibular movement path 2-1 and opposite lateral mandibular movement paths 2-2 extending from an apex 2 on a recording or tracing plate 1. The reason why movement paths defining longitudinal and lateral mandibular movements are called "Gothic arch tracings" is because when a mandibular movement involving a forward longitudinal mandibular movement defined by the path 2-1 and opposite lateral mandibular movements defined by the paths 2-2 is figured on the tracing plate 1, the traced figure of the mandibular movement has a Gothic arch shape. The apex 2 is regarded as a starting point of the longitudinal and lateral mandibular movements. When a tracing stylus, which is attached to the mandible, as described hereinafter, is positioned at the apex 2, it is considered that a centric relation is established.

For a partially edentulous patient who is edentulous on the maxilla or mandible or a fully edentulous patient who is edentulous on both the maxilla and mandible, the centric relation of the mandible corresponds to the apex of a horizontal Gothic arch traced in accordance with an intrinsic vertical dimension of the patient. In this case, accordingly, a centric occlusion may be formed at the apex of the horizontal Gothic arch trace.

For a fully dentulous patient who is dentulous on both the maxilla and mandible, the horizontal centric relation of the mandible should be traced under the condition in which the maxillary and mandibular dentitions are spaced from each other to open the oral cavity, thereby preventing a stylus, which is used to record a Gothic arch trace of the patient, from coming into contact with a tooth of the patient during a tracing operation thereof. In other words, the tracing of the centric relation should be carried out with a vertical dimension elevated from an intrinsic vertical dimension of the patient.

In this case, however, the centric relation may vary in position on a tracing plate mounted to the maxilla due to a difference between the vertical dimension used and the intrinsic vertical dimension. In order to eliminate such a positional variation of the centric relation, the stylus should have a certain forward inclination corresponding to an angle of hinge rotation along the jaw movement path of the patient opening and closing the oral cavity while being in contact with the tracing plate in a state perpendicular to the tracing plate.

Meanwhile, if the position and orientation of the stylus mounted to the mandible is inaccurate with respect to the horizontal plane of the dentition, namely, the occlusal plane, that is, if the stylus is not in parallel to the occlusal plane, then it is in a laterally inclined state with respect to the maxilla. In such a state, it is impossible to expect an accurate centric relation tracing. Prior to a description associated with the mounted state of the stylus, the structure of the mandible will be described in conjunction with FIGS. 2a to 2e. FIG. 2a is a perspective view illustrating the structure of a mandible, FIG. 2b is a side view illustrating the maxilla denoted by the reference numeral 31, FIG. 2c is a bottom view of the maxilla 31, FIG. 2d is a side view illustrating an edentulous mandible, and FIG. 2e is a bottom view of the mandible shown in FIG. 2d. The mandible, which is denoted by the reference numeral 3, is hingably coupled to the maxilla 31 about a horizontal reference axis 3-1 (FIGS. 2a and 3). Teeth (dentition) 4 are fixed to the mandible 3. The horizontal reference axis 3-1 defines a Bonwill triangle 3-2, along with a central incisor edge between two mandibular central incisors. The Bonwill triangle 3-2 is indicated by a shaded portion in FIG. 2a. The horizontal plane of the dentition 4 defines an occlusal plane 3-3. A vertical plane extending vertically through the front central portion of the dentition 4 is called a "mid-sagittal plane". This mid-sagittal plane is denoted by the reference numeral 3-4. A stylus 5 is mounted at a cross point 3-5 between the center of opposite mandibular first molars and the mid-sagittal plane 34.

Typically, the mandible 3 has a structure shown in FIG. 3. As shown in FIG. 3, the Bonwill triangle 3-2, which is a triangle extending from the horizontal reference axis 3-1 of the mandible 3 to the front central point of the dentition 4, defines a certain angle 3-6 along with the horizontal plane of the dentition 4, namely, the occlusal plane 3-3. This angle is called a "Balkwill angle".

For dentulous patients, the stylus 5 is mounted in such a fashion that its tip is positioned at the cross point 3-5 shown in FIG. 2a while being forwardly inclined with reference to a vertical plane orthogonal to the Bonwill triangle 3-2 by an angle corresponding to the Balkwill angle 3-6, as shown in FIG. 4. Generally, the stylus 5 is mounted in such a fashion that the inclination angle thereof, namely, the angle defined by the stylus 5 forwardly inclined from a line perpendicular to the occlusal plane 3-3 of the mandible, is 17° in average. Theoretically, it is desirable for the stylus 5 to be inclined by an angle corresponding to the Balkwill angle 3-6. For some patients who do not conduct a regular mandibular hinge movement about the horizontal reference axis 3-1, however, it is necessary to adjust the angle of the stylus 5 without limiting it to 17° in order to allow the stylus 5 to be positioned on a patient's hinge movement path, for example, at a point B1 or B2. Referring to FIG. 5, the stylus 5 is mounted to the dentition 4 of the mandible. As shown in FIG. 6, the stylus 5 is threadedly coupled to a support plate 6. A pair of wing plates 7 are threadedly coupled to opposite lateral ends of the support plate 6 by means of screws 8, respectively. The wing plates 7 are also fixedly mounted to opposite portions of the dentition on the mandible by means of coupling members 9 fixed to the wing plates 7 and wires 10 coupled to the coupling members 9, respectively. As shown in FIG. 6, the stylus 5 includes a bolt body 5-4 threadedly coupled to the support plate 6, and a nut body 5-21 threadedly coupled to the upper end of the bolt body 5-4. A spring pin 5-2 is slidably mounted in the bolt body 5-4 in such a fashion that its tip 5-1 is vertically protruded through the nut body 5-21 coupled to the bolt body 5-4. The spring pin 5-2 is always urged by a spring 5-3 so that it slide upwardly. The stylus 5 having such a configuration is mounted in such a manner that its tip; namely, the tip 5-1, is positioned on an extension line between the opposite mandibular first molars (denoted by the reference numeral 4-1 in FIG. 9a) while being in an inclined state. In other words, the bolt body 5-4 of the stylus 5 is threadedly coupled to the support plate in a state inclined with respect to the support plate 6. Also, the nut body 5-2 of the stylus 5 is threadedly coupled to the bolt body 5-4 in a state inclined with respect to the support plate 6. For this reason, the support plate 6 should be provided with a guide groove 6-1 for receiving a portion of the nut body 5-2 of the stylus 5 further downwardly protruded than other portions of the nut body 5-2 during the inclined coupling of the nut body 5-2, as shown in FIG. 6. Due to the provision of the guide groove 6-1, the stylus 5 coupled to the support plate 6 has a coupling portion having a length corresponding to only a distance L1 at one side thereof. As a result, the stylus 5 exhibits a reduced coupling force to the support plate 6, so that it may be loose. In this case, errors may be generated in the tracing of a Gothic arch for obtaining an accurate centric relation of the mandible. In practical cases, a dental pattern of a patient is first copied. A dental cast is then formed using plaster, based on the copied dental pattern. Thereafter, the dental cast is mounted to a general articulator in such a fashion that it conforms to a dentition of the patient. A tracing device, which is denoted by the reference numeral 20 in FIG. 5, is then assembled to the dentition of the articulator. Subsequently, the nut body 5-21 is threadedly coupled to the bolt body 5-4, as shown in FIG. 6. A cap 11, which is provided at its upper surface with an upwardly protruded pin 11-1, is then mounted on the nut body 5-21, as shown in FIG. 7. A tracing plate 1 is laid on the cap 11 in such a fashion that it is supported by the pin 11-1. Thereafter, a binding material 1-1, which has a property of being set within several minutes, is then applied to a palatal surface portion of the articulator facing the cap 11. The maxilla 31 of the articulator is then depressed in such a fashion that the tracing plate 1 is settled in the binding material 1-1, as shown in FIG. 7. In this state, the articulator is kept for several minutes until the binding material 1-1 is set. After the setting of the binding material 1-1, the maxilla 31 of the articulator is separated from the mandible 3 (not shown in FIG. 7). As a result, the stylus 5 and cap 11 are separated from the tracing plate 1. Of course, the tracing plate 1 is maintained in a state attached to the maxilla 31. Thereafter, the cap 11 is separated from the stylus 5. The cap 11 and tracing plate 1 may have configurations shown in FIG. 8, respectively. Referring to FIG. 8, the tracing plate 1 has a pin receiving hole 1-2 for receiving the pin 11-1 of the cap 11 so that it can be coupled to the cap 11. The tracing plate 1 is also provided at its front rear ends with coupling protrusions 1-3 formed integrally with the tracing plate 1. The coupling protrusions 1-3 have a construction upwardly bent from the horizontal tracing plate 1 so that they have an increased area contacting the binding material 1-1. Next, the tracing device 20 of FIG. 5 and the tracing plate 1 of FIG. 7, to which the set binding material 1-1 is integrally coupled, are completely separated from the articulator which is a dental model having maxillary and mandibular casts conforming to the maxilla and mandible of the patient. The separated tracing device 20 and tracing plate 1 are then mounted to the maxilla and mandible of the patient. Under this condition, the mandible of the patient moves longitudinally and laterally, thereby causing a Gothic arch trace to be formed on the tracing plate 1, as shown in FIG. 1. The tracing plate 1 recorded with the Gothic arch trace is then separated from the mouth of the patient, together with the set coupling material 1-1. A separate disc, which has a hole corresponding to the apex 2 of the Gothic arch trace, is subsequently attached to the tracing plate 1 in such a fashion that its hole is vertically aligned with the apex 2 of the Gothic arch trace. Thereafter, the tracing plate 1 attached with the disc and the tracing device 20 are fixed again to the maxillary and mandibular dentitions in the oral cavity of the patient. In this state, a bite material is put on desired portions of the maxilla and mandible between the tracing device 20 and tracing plate 1. After the bite material is set, the resulting structure including the maxillary and mandibular models and the set bite material is mounted again to the articulator in such a fashion that it has a centric relation conforming to the centric relation obtained in the oral cavity of the patient. Using this articulator, a dental prothesis is carried out while maintaining a stable centric occlusion. The above mentioned method is particularly useful for fully dentulous patients and partially dentulous patients. Even for patients exhibiting an unclear centric relation, in particular, patients who have used dentures for a lengthened period of time, an accurate centric relation can be obtained using the above mentioned method. However, the tracing device used in such a method may involve a problem in that the stylus may be pierced into the tongue of the patient due to an unstable positioning of the tracing plate. Furthermore, the tracing may be inaccurately carried out because the tracing plate has no lateral symmetry in a horizontal direction. In addition, it is difficult to accurately mount the tracing device to the articulator.

Conventional articulators for fully edentulous patients are disclosed in U.S. Pat. Nos. 4,273,533 and 4,279,595. Such articulators have a configuration including a tracing device adapted to be mounted to the maxilla, and a tracing plate adapted to be mounted to the mandible. However, such conventional articulators can be used only for edentulous patients. Furthermore, they have a limited applicability because they use a stylus constructed to extend vertically.

SUMMARY OF THE INVENTION

Therefore, an object of the invention is to solve the above mentioned problems involved in the prior art, and to provide an apparatus for tracing a centric relation of a mandible including a stylus seated on a ball in such a fashion that it pivots in vertical, longitudinal, and lateral directions, thereby being capable of conveniently adjusting its position and orientation so that it is set to conform to a hinge movement of a patient, the ball having a cylindrical upper portion adapted to reduce an instability of the stylus during a tracing operation thereof.

For a dentulous patient, a stylus, which is used to record a Gothic arch trace of the patient, may come into contact with a tooth of the patient during a tracing operation thereof, thereby interfering with a jaw movement of the patient. To this end, the jaw movement should be conducted with a vertical dimension adjusted to be larger than an intrinsic vertical dimension of the patient. In other words, the apex of a Gothic arch is traced in accordance with an elevated vertical dimension. On the other hand, a maxillary-mandibular jaw relation should be obtained by setting a bite material under the condition in which the vertical dimension is lowered to be approximate to the intrinsic vertical dimension of the patient as much as possible. Where the bite material used has a greater thickness, there is a greater difference between the maxillary-mandibular jaw relation obtained in the case in which the tracing apparatus is mounted in the oral cavity of the patient and the maxillary-mandibular jaw relation obtained in the case in which the tracing apparatus is mounted to an articulator. Also, the apex of the Gothic arch traced on the tracing plate should be fixed in spite of an elevated or lowered vertical dimension. In order to meet such requirements, the present invention provides an apparatus for tracing a centric relation of a mandible in which a stylus is coupled to a nut-shaped ball supported by a base plate having a size seated in a space defined by a dentition and supported by support members engaged with the dentition, and a support plate threadedly coupled to the base plate in such a fashion that it can be selectively pivotable, so that the stylus can be adjusted in position and orientation to be used for both dentulous and fully edentulous patients.

In accordance with the present invention, the following effects are provided.

First, the stylus can be inclined along a patient's hinge movement path, Accordingly, a constant apex of a Gothic arch is traced even when a vertical maxillary-mandibular jaw relation varies.

Second, it is possible to arrange the tracing plate in parallel to a maxillary horizontal plane while being laterally balanced. This can be more accurately and conveniently achieved by use of a mounting reference die according to the present invention.

Third, the stylus can be easily and conveniently adjusted in position and orientation by virtue of the base plate and support plate threadedly coupled to each other. After the adjustment, the stylus can be easily fixed in position and orientation by use of a setable binding material.

Fourth, for fully edentulous patients, the tracing apparatus of the present invention can be used to directly correct the occlusal relation in the oral cavity. For fully edentulous patients, tracing of a horizontal maxillary-mandibular jaw relation (the apex of a Gothic arch) can be carried out without involving any variation in the vertical dimension, that is, with an intrinsic vertical dimension of a patient. This is because fully edentulous patients have no tooth possibly interfering with the stylus during the tracing operation of the stylus. In accordance with the present invention, the stylus is fitted in a pin hole formed at the mounting reference die which, in turn, is arranged approximately in parallel to a mandibular occlusal plane. As a result, the stylus is fixed in perpendicular to the mandibular occlusal plane. In this state, a crap, which carries the tracing plate and serves as a transfer plate, is fitted on the fixed stylus. Using the cap, the tracing plate is then mounted to the maxilla. After separating the cap from the stylus, the tracing plate is adjusted in orientation so that it is parallel to the horizontal maxillary occlusal plane. Thereafter, the cap is fitted again on the stylus and then adjusted in orientation by slightly unfastening screws adapted to fix the stylus, thereby allowing the cap to be in parallel to the tracing plate. In this state, the cap and tracing plate are bonded together. Subsequently, the stylus is adjusted in orientation so that it is perpendicular to the tracing plate. After this adjustment, the stylus is fixed by fastening the screws.

In accordance with one aspect, the present invention provides an apparatus for tracing a centric relation of a mandible comprising a stylus arranged at a point, where an occlusal plane and a mid-sagittal plane cross a line extending between central fossae of mandibular first molars, and a tracing plate adapted to be mounted to a maxilla at a region corresponding to the stylus, further comprising: a ball threadedly coupled to said stylus in such a fashion that it is fitted around said stylus in the form of a nut and cylinder; a base plate having a circular hole provided with an arc-shaped surface serving as a seat for said ball; a support plate arranged over said base plate and coupled to said base plate while being vertically spaced from said base plate, said support plate having a circular hole provided with an arc-shaped surface cooperating with said arc-shaped surface of said base plate to clamp said ball therebetween when said support plate is in a state coupled to said base plate; and a plurality of support members each mounted to a desired portion of said base plate at one end thereof and engaged with a desired surface portion of a dentition at the other end thereof, thereby maintaining said base plate at a desired position.

In accordance with another aspect, the present invention provides a mounting reference die for a tracing plate included in a Gothic arch tracing apparatus comprising: a die plate; a pin hole formed through said die plate and adapted to receive a tip of a stylus included in said tracing apparatus; a plurality of longitudinally spaced lateral horizontal lines formed on an upper surface of said die plate and adapted to measure a lateral inclination of said tracing plate with respect to an occlusal plane; a plurality of parabolic horizontal lines formed on said upper surface of said die plate to have parabolic shapes of different sizes conforming to those of different patients' dentitions defined on said occlusal plane, respectively, each of said parabolic horizontal lines being laterally symmetric with respect to the center thereof; a front depth measuring bar downwardly protruded from a lower surface of said die plate and arranged at a front portion of said die plate on a center line extending through the centers of said lateral horizontal lines while being orthogonal to said lateral horizontal lines; a rear depth measuring bar serving as a vertical adjustment bar and being upwardly protruded from said upper surface of said die plate in rear of said front depth measuring bar, said rear depth measuring bar serving to measure a depth of a maxilla in cooperation with said front depth measuring bar; a plurality of lateral depth measuring holes formed through said die plate at opposite ends of said parabolic horizontal lines in such a fashion that they are laterally symmetric with respect to said center line; a pair of lateral depth measuring bars fitted in two laterally symmetric ones of said lateral depth measuring holes selected in accordance with the size of said maxilla, said lateral depth measuring bars serving to measure a depth of said maxilla at opposite lateral ends of said oral cavity, respectively; a bolt hole formed through a central portion of said die plate; and a guide bolt vertically inserted into said bolt hole and adapted to establish an accurate lateral horizontal relation of said tracing plate with respect to said maxilla, said guide bolt including a clamp bolt inserted into said bolt hole, a pair of clamp nuts threadedly coupled to said clamp bolt at opposite sides of said die plate, respectively, to clamp said die plate in a state perpendicular to said clamp bolt, and a horizontal guide surface formed at a head portion of said clamp bolt and adapted to maintain said tracing plate in parallel to said die plate.

BRIEF DESCRIPTION OF THE DRAWINGS

Other objects and aspects of the invention will become apparent from the following description of embodiments with reference to the accompanying drawings in which:

FIG. 13b is an exploded cross-sectional view illustrating the stylus shown in FIG. 13a; and FIG. 13c is a cross-sectional view illustrating an in-use state of the stylus of FIG. 13a.

DESCRIPTION OF THE PREFERRED EMBODIMENTS

Figure 9A:
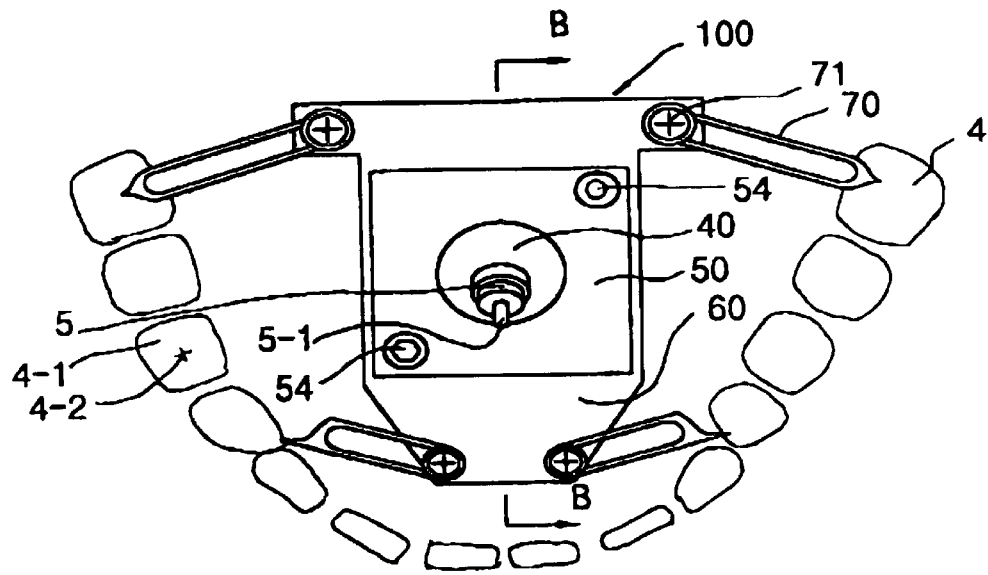
FIG. 9a is a plan view illustrating a tracing apparatus of the present invention which is applied to a dentulous patient.

FIG. 9a is a plan view illustrating a tracing apparatus of the present invention which is applied to a dentulous patient.

In FIG. 9a, the tracing apparatus is denoted by the reference numeral 100. Referring to FIG. 9a, a ball 40 is illustrated which is centrally arranged on a line extending between the central fossae 4-2 of mandibular first molars 4-1 in a dentition 4. The ball 40 has a nut-shaped construction. A stylus 5 is threadedly coupled to the ball 40. The ball 40 is seated on a seat portion of a base plate 60. A support plate 50 is fitted around the ball 40 seated on the base plate 60. The support plate 50 is coupled to the base plate 60 by means of screws 54 while being upwardly spaced from the base plate 60. As the screws 54 are tightened, the ball 90 is firmly clamped between the support plate 50 and base plate 60. The base plate 60 is arranged inside the dentition 4 in the oral cavity and mounted to the dentition 4 by means of support members 70. Each of the support members 70 is threadedly coupled to one of corners of the base plate 60 by means of a screw 71 at one end thereof while being engaged with a desired surface portion of the dentition 4 at the other end thereof.

Figure 9B:
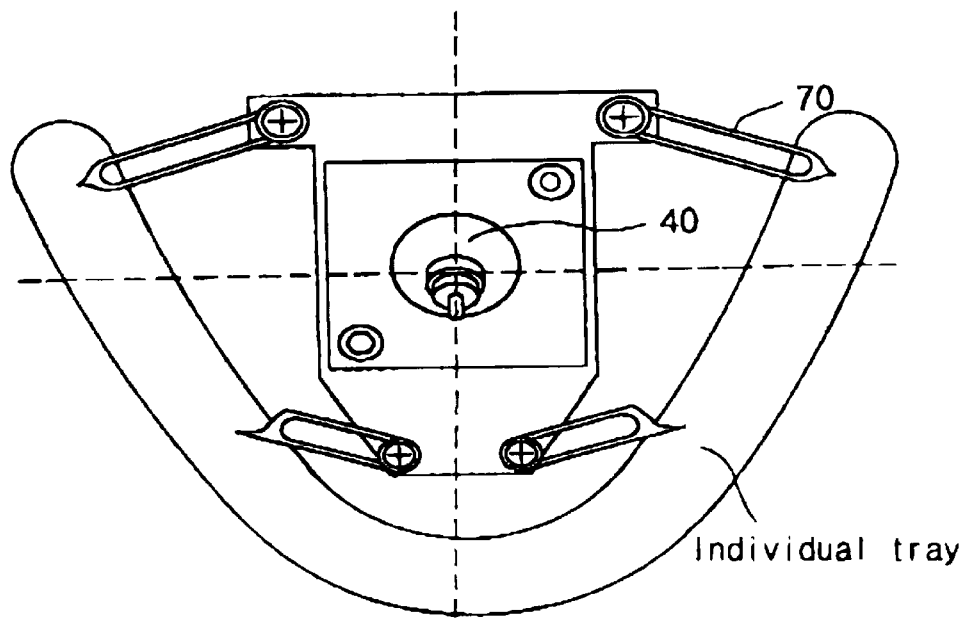
FIG. 9b is a plan view illustrating the tracing apparatus of the present invention which is applied to an edentulous patient.

FIG. 9b is a plan view illustrating the tracing apparatus 100 of the present invention which is applied to an edentulous patient. In this case, the ball 40 is arranged at a position similar to that in the case for a dentulous patient, as shown in FIG. 9b. The position of the ball 40 corresponds to a point at which the mid-sagittal plane 3-4 crosses a line extending between the central fossae 4-2 of mandibular first molars 4-1. The support members 70 are mounted to a tray prepared for an individual patient at four positions so that the position of the ball 40 is fixed. Such a tray is called an "individual tray".

Figure 10A:
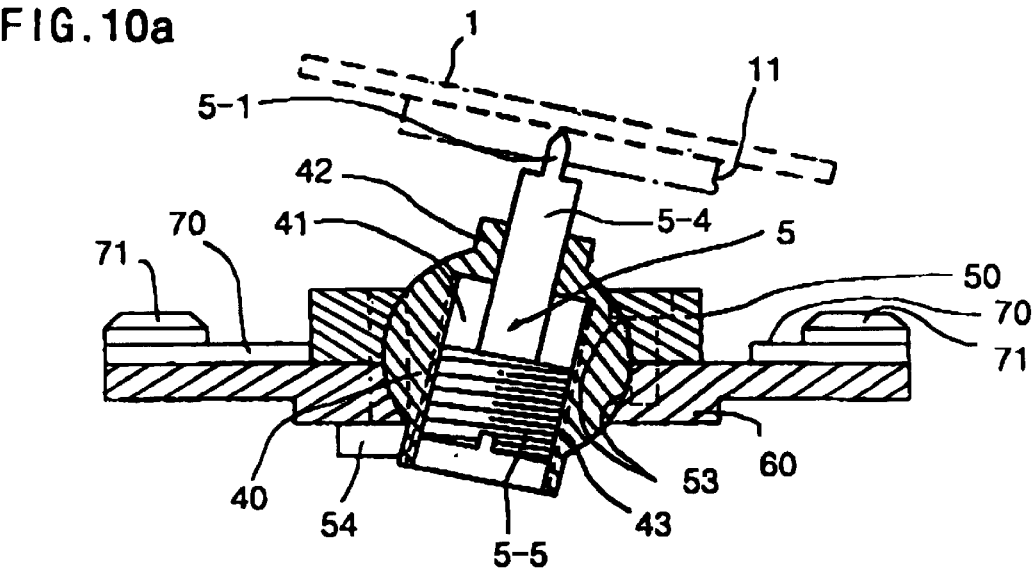
FIG. 10a is an enlarged cross-sectional view taken along the line B—B of FIG. 9a;.

FIG. 10a is an enlarged cross-sectional view taken along the line B—B of FIG. 9a. As shown in FIG. 10a, the stylus 5 includes a stylus body consisting of a tip portion 5-1, a rod portion 5-4, and a threaded portion 5-5. The tip portion 5-1 extends upwardly from an upper end of the rod portion 5-4 whereas the threaded portion 5-5 extends downwardly from a lower end of the rod portion 5-4. In this case, the tip portion 5-1 and threaded portion 5-5 are integral with the rod portion 5-4. The stylus 5 is threadedly coupled to the nutshaped ball 40 at its threaded portion 5-5. As shown in FIG. 10a, the support plate 50 and base plate 60 have circular holes 53 provided with arc-shaped surfaces and adapted to receive the ball 40. The support plate 50 and base plate 60 are coupled together by means of the screws 54 while being vertically spaced from each other under the condition in which the ball 40 is fitted in the circular holes 53. As the screws 54 are tightened, the ball 40 is firmly clamped between the support plate 50 and base plate 60. The ball 40 has a cylindrical recess 41 having a threaded portion 43 adapted to be threadedly coupled with the threaded portion 5-5 of the stylus 5. The cylindrical recess 41 is open at its upper end to allow the rod portion 5-4 of the stylus 5 to extend upwardly and outwardly from the ball 40. A tubular skirt 42 is formed at the upper end of the ball 40. The tubular skirt 42 has an inner diameter equal to the upper opening of the cylindrical recess 41 and serves to prevent the stylus 5 to be loose during its Gothic arch tracing operation. Referring to FIG. 10a, a cap 11 is also illustrated. The cap 11, which serves as a transfer plate, is fitted around the tip portion 5-1 of the stylus 5 so as to support a tracing plate 1.

Figure 10B:
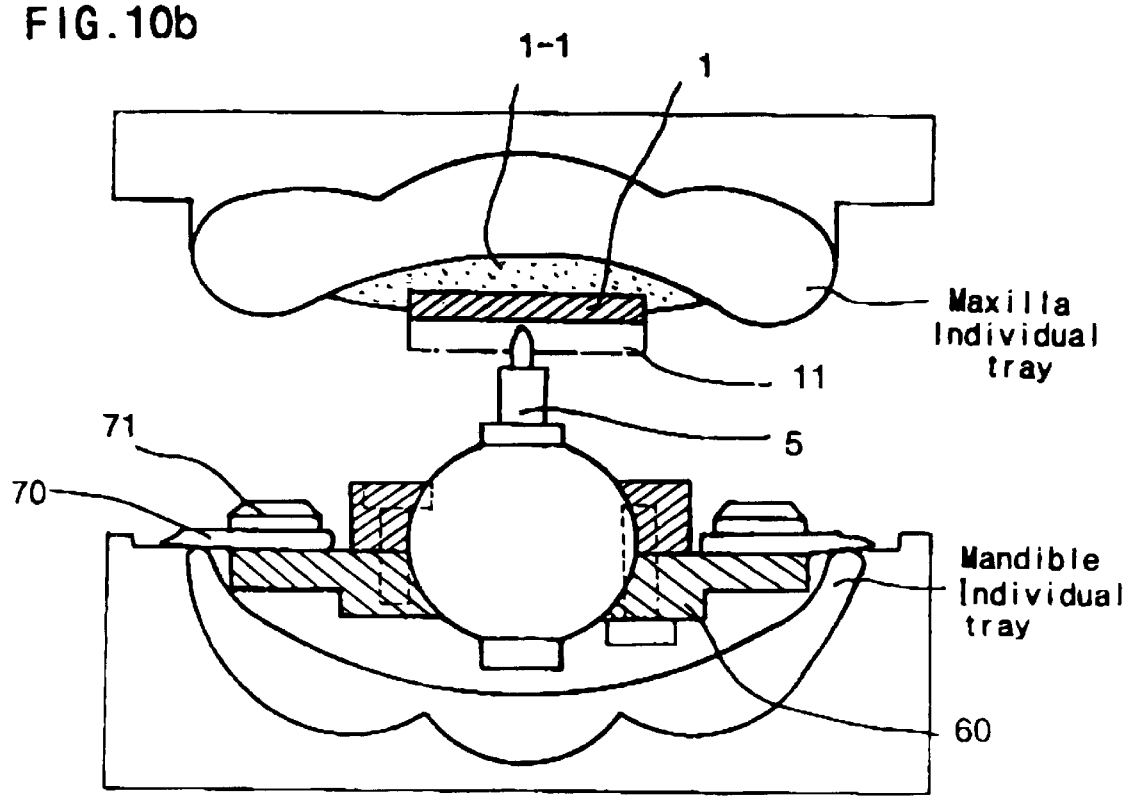
FIG. 10b is a cross-sectional view illustrating a state in which the tracing apparatus of the present invention is used for an edentulous patient.

FIG. 10b is a cross-sectional view illustrating a state in which the tracing plate is arranged in parallel to a maxillary occlusal plane in the oral cavity of an edentulous patient. A maxillary tray is mounted to the maxilla, and a mandible tray is mounted to the mandible. As shown in FIG. 10b, the tracing plate 1 is horizontally attached to the maxillary occlusal plane by means of a binding material 1-1. The stylus 5 is fitted in the tracing plate 1 in such a fashion that it extends perpendicularly to the tracing plate 1. The base plate 60, which supports the stylus 5, is mounted to the mandibular tray at four corners thereof by the support members 70.

Figure 11:
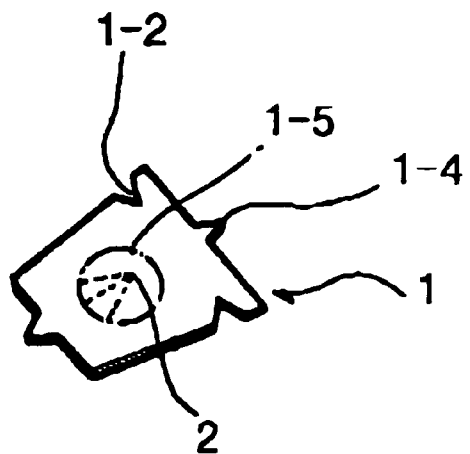
FIG. 11 is a perspective view illustrating a tracing plate used in accordance with the present invention.

FIG. 11 is a perspective view illustrating the tracing plate 1 used in accordance with the present invention. As shown in FIG. 11, the tracing plate 1 is provided at its front and rear surfaces with coupling protrusions 1-4, respectively. The tracing plate 1 is also provided with pin receiving grooves 1-2 at opposite side surfaces thereof, respectively. For dentulous patients, the tracing plate 1 is mounted in such a fashion that it is forwardly inclined by a certain forward angle (about 17°) with respect to a line perpendicular to the occlusal plane of the mandible. For edentulous patients, the tracing plate 1 is mounted in such a fashion that it is parallel to the occlusal plane of the maxilla. The tracing plate 1 is adjusted in lateral inclination by a separate mounting reference die. This will be described hereinafter.

Figure 12A:
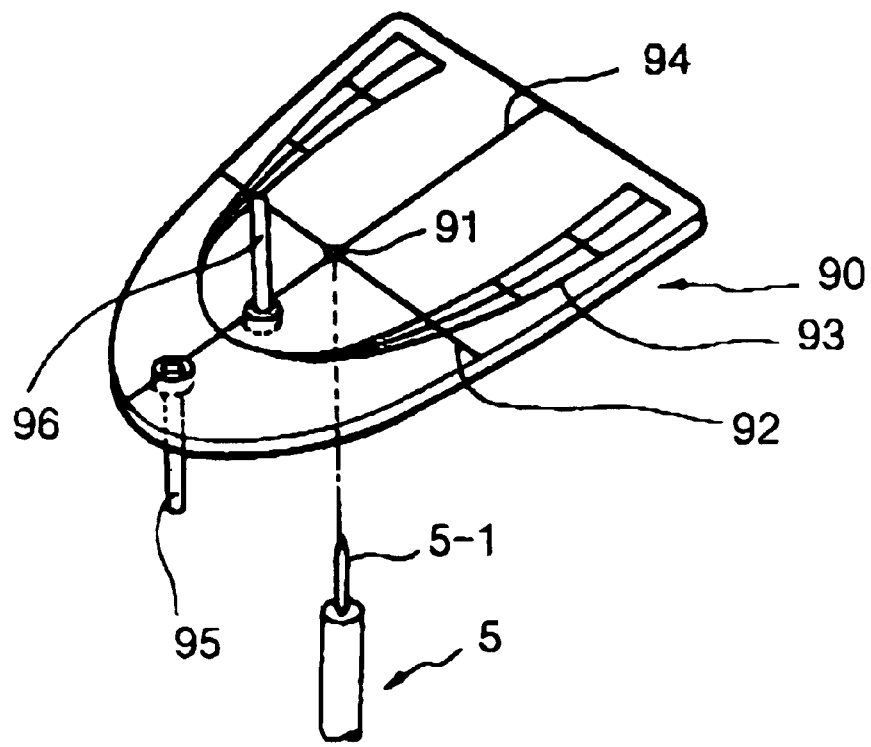
FIG. 12a is a perspective view illustrating a mounting reference die according to an embodiment of the present invention.

FIG. 12a is a perspective view illustrating a mounting reference die adapted to mount the tracing apparatus 100 of the present invention in an accurately balanced state. In accordance with an embodiment of the present invention, the mounting reference die, which is denoted by the reference numeral 90 in FIG. 12a, has a plate shape and serves to allow an easy adjustment of the tracing apparatus 100 for aligning the tip portion 5-1 of the stylus 5 with the center of the mandibular model.

As shown in FIG. 12a, the mounting reference die 90 has a pin hole 91 for receiving the tip portion 5-1 of the stylus 5. A plurality of longitudinally spaced lateral horizontal lines 92 are formed on an upper surface of the mounting reference die 90. The lateral horizontal lines 92 are adapted to measure a lateral inclination of the tracing plate 1 with respect to the occlusal plane. A plurality of parabolic horizontal lines 93 are also formed on the upper surface of the mounting reference die 90. The parabolic horizontal lines 93 have parabolic shapes of different sizes conforming to those of different patients' dentitions, which may be on the occlusal plane shown in FIG. 2a, 2b, 2d, or 3, respectively. A front depth measuring bar 95 is downwardly protruded from a lower surface of the mounting reference die 90. The front depth measuring bar 95 is arranged at the front portion of the mounting reference die 90 on a line 94 extending through the center of the lateral horizontal line 92 while being orthogonal to the lateral horizontal line 92. A vertical adjustment bar 96, which is a rear depth measuring bar, is upwardly protruded from the upper surface of the mounting reference die 90 in rear of the front depth measuring bar 95. The front depth measuring bar 95 and vertical adjustment bar 96 serve to measure the depth of the maxillary oral cavity.

Figure 12B:
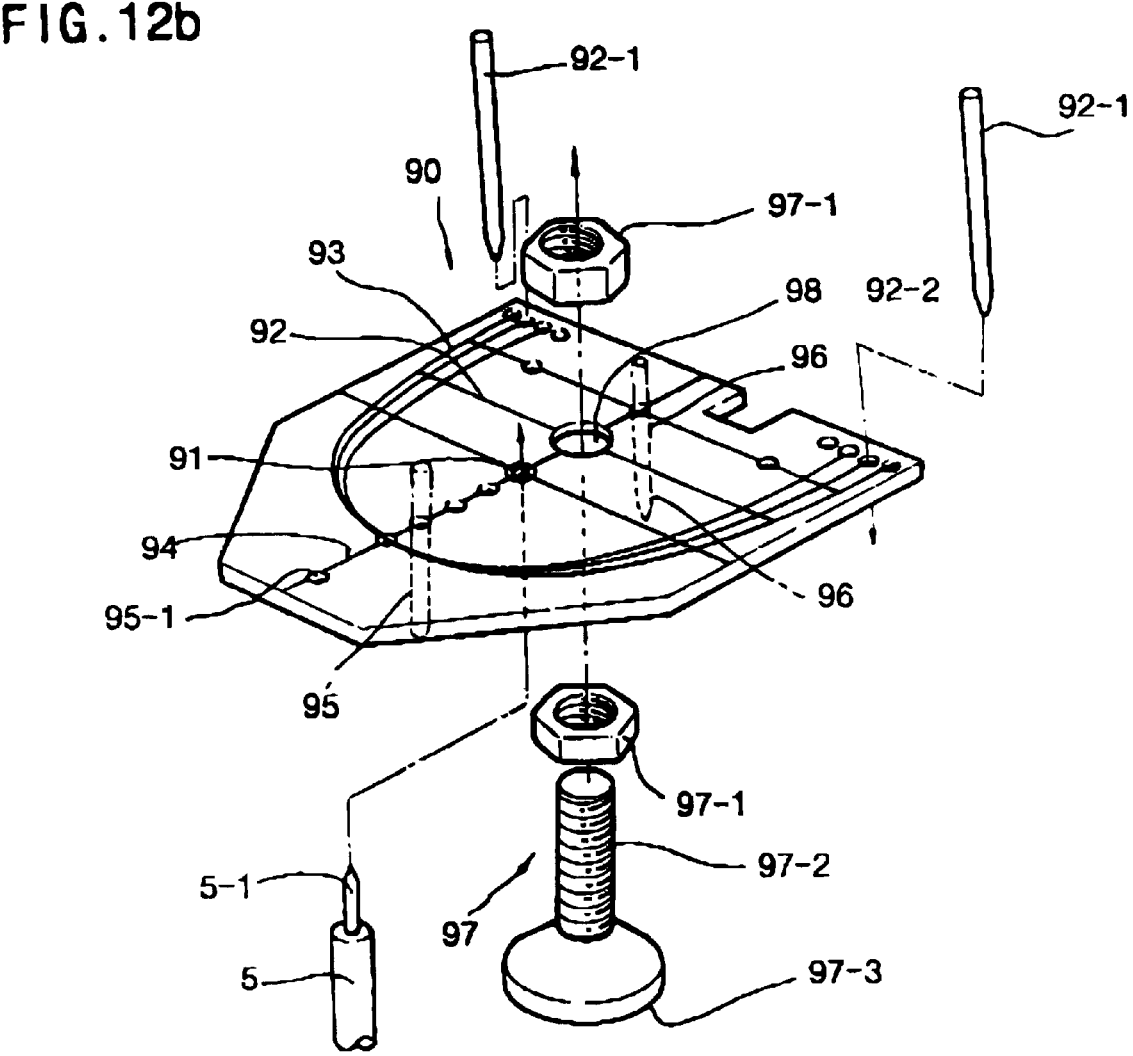
FIG. 12b is an exploded perspective view illustrating a mounting reference die according to another embodiment of the present invention.
Figure 12C:
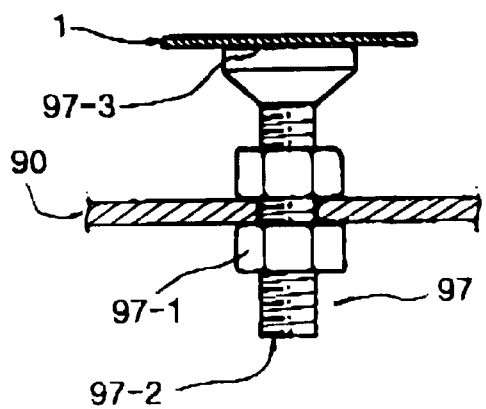
FIG. 12c is an assembled perspective view illustrating the mounting reference die shown in FIG. 12b.

FIG. 12b is an exploded perspective view of a mounting reference die to be used for dentulous patients in accordance with another embodiment of the present invention. FIG. 12c is a cross-sectional view illustrating an in-use state of the mounting reference die 90. In FIGS. 12b and 12c, the elements respectively corresponding to those in FIG. 12a are denoted by the same reference numerals. As shown in FIG. 12b, the mounting reference die has a pin hole 91 for receiving the tip portion 5-1 of the stylus 5. A plurality of longitudinally spaced lateral horizontal lines 92 are formed on an upper surface of the mounting reference die 90. The lateral horizontal lines 92 are adapted to measure a lateral inclination of the tracing plate 1 with respect to the occlusal plane. A plurality of parabolic horizontal lines 93 are also formed on the upper surface of the mounting reference die 90. The parabolic horizontal lines 93 have parabolic shapes of different sizes conforming to those of different patients' dentitions, which may be on the occlusal plane shown in FIG. 2a, 2b, 2d, or 3, respectively. A front depth measuring bar 95 is downwardly protruded from a lower surface of the mounting reference die 90. The front depth measuring bar 95 is arranged at the front portion of the mounting reference die 90 on a line 94 extending through the centers of the lateral horizontal lines 92 while being orthogonal to the lateral horizontal lines 92, A vertical adjustment bar 96, which is a rear depth measuring bar, is upwardly protruded from the upper surface of the mounting reference die 90 in rear of the front depth measuring bar 95, The front and rear depth measuring bars 95 and 96 serve to measure the depth of the maxillary oral cavity. The front and rear depth measuring bars 95 and 96 define a longitudinal reference line for left and right lateral depth measuring bars 92-1. A plurality of longitudinally spaced holes 95-1 are formed through the mounting reference die 90 along the line 94. The front depth measuring bar 95 is fitted in one of the holes 95-1 selected in accordance with the size of the patient's maxilla. A plurality of lateral depth measuring holes 92-2 are also formed through the mounting reference die 90 at opposite ends of the parabolic horizontal lines 93 in such a fashion that they are laterally symmetric with respect to the line 94. The left and right lateral depth measuring bars 92-1 are fitted in two laterally symmetric lateral depth measuring holes 92-2 selected in accordance with the size of the patient's maxilla, respectively. A bolt hole 98 is formed at the central portion of the mounting reference die 90, A guide bolt 97 is vertically inserted into the bolt hole 98. The guide bolt 97 serves to establish an accurate lateral horizontal relation of the tracing plate 1 with respect to the maxilla. The guide bolt 97 includes a clamp bolt 97-2 inserted into the bolt hole 98. A pair of clamp nuts 97-1 are threadedly coupled to the clamp bolt 97-2 at opposite sides of the mounting reference die 90, respectively, in order to clamp the mounting reference die 90 in a state perpendicular to the clamp bolt 97-2. A horizontal guide surface 97-3 is formed at a head of the clamp bolt 97-2 in order to maintain the tracing plate 1 in parallel to the mounting reference die 90. In this configuration of the mounting reference die 90, the front and rear depth measuring bars 95 and 96 define a longitudinal reference line which is aligned with the mid-sagittal plane. The left and right lateral depth measuring bars 92-1 are arranged in such a fashion that they are laterally spaced from the longitudinal reference line by the same distance and upwardly protruded by the same length, so that their upper ends are placed on a maxillary horizontal plane. Accordingly, the plane of the mounting reference die 90 is parallel to the maxillary horizontal plane while being laterally balanced with respect to the patient's mid-sagittal plane. As a result, the tracing plate 1, which is attached to the horizontal guide surface 97-3 arranged in parallel to the mounting reference die 90, is maintained in a laterally balanced or symmetric state without being laterally inclined.

Figure 13A:
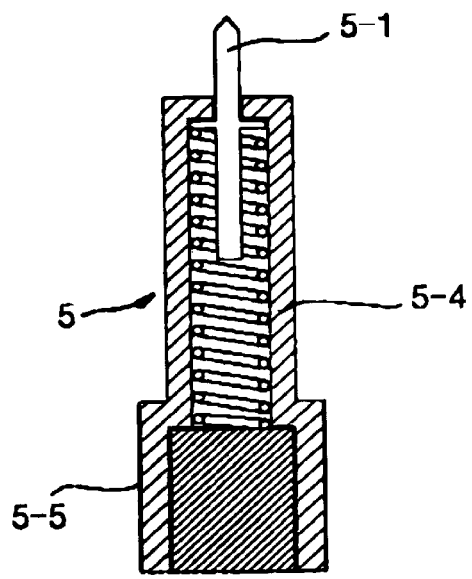
FIG. 13a is an assembled cross-sectional view illustrating a stylus according to another embodiment of the present invention.
Figure 13B:
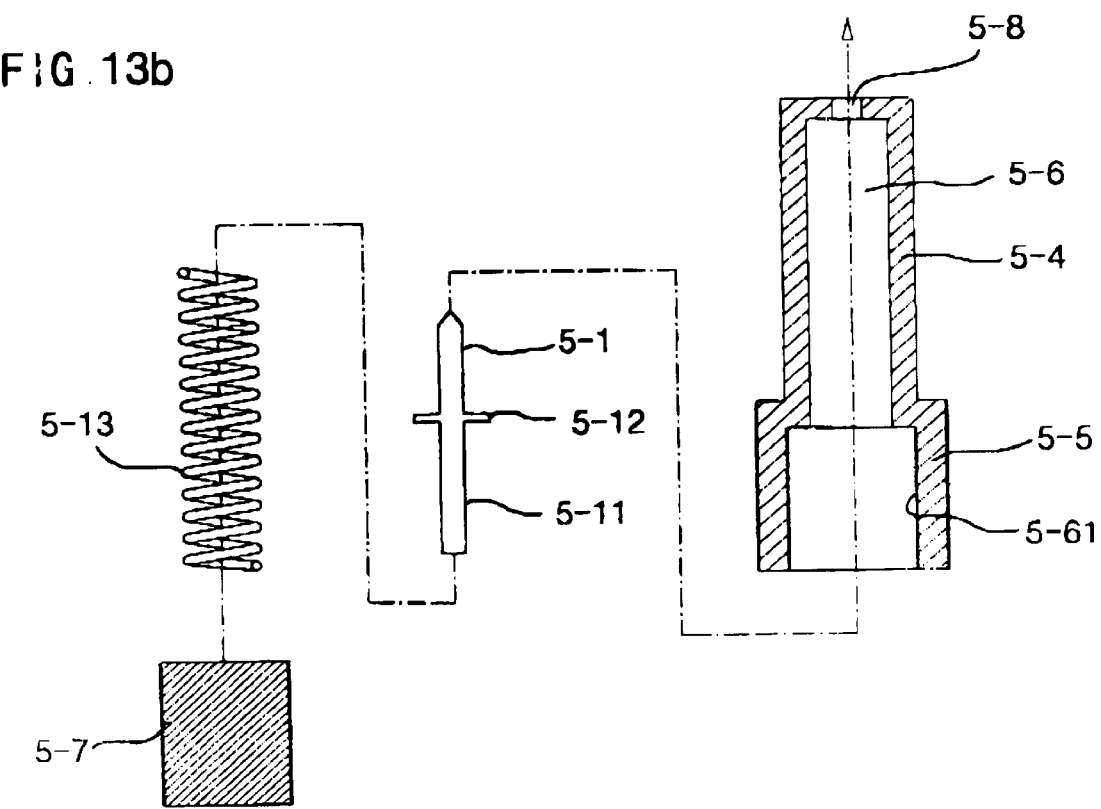

FIGS. 13a and 13b illustrate a stylus, which is used to directly correct the occlusal relation in the oral cavity of a dentulous or fully edentulous patient who has disturbances of the temporomandibular joint, in accordance with another embodiment of the present invention. FIG. 13a is an assembled cross-sectional view whereas FIG. 13b is an exploded cross-sectional view. In FIGS. 13a and 13b, the elements respectively corresponding to those of FIG. 10a are denoted by the same reference numerals. In this case, the tip portion 5-1 comprises a tip member independent of the rod portion 5-4. The tip member 5-1 is mounted in the interior of the rod portion 5-4 while extending upwardly through an upper end of the rod portion 5-4. As shown in FIGS. 13*a* and 13*b*, the rod portion 5-4 of the stylus 5 has a hollow structure defined with an inner space 5-6 for receiving the pin member 5-1. The rod portion 5-4 is also provided at its upper end with a guide hole 5-8 for guiding a vertical movement of the pin member 5-1. The guide hole 5-8 communicates with the inner space 5-6 of the rod portion 5-4. The pin member 5-1 has a downward extension 5-11 and a stopper 5-12. A compression coil spring 5-13 is disposed in the inner space 5-6 of the rod portion 5-4 in such a fashion that it is in contact with the stopper 5-12 at one end thereof and with a plug member 5-7 at the other end thereof. The plug member 5-7 is threadedly coupled to inner threads 5-61 of the threaded portion 5-5 in such a fashion that it supports the lower end of the compression coil spring 5-13. By such a configuration, the pin member 5-1 is always urged in an upward direction by the compression coil spring 5-13.

Figure 1:
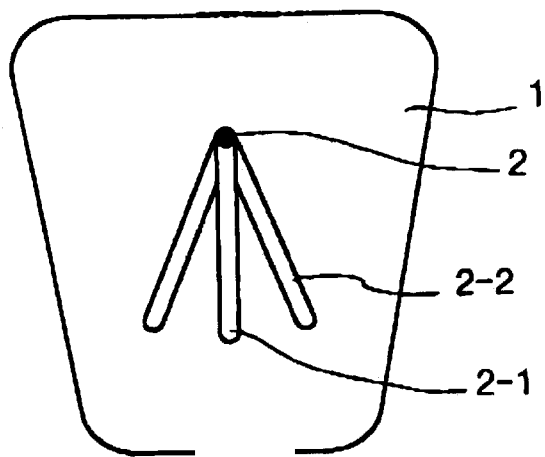
FIG. 1 is schematic view illustrating Gothic arch traces recorded on a general tracing plate.
Figure 2A:
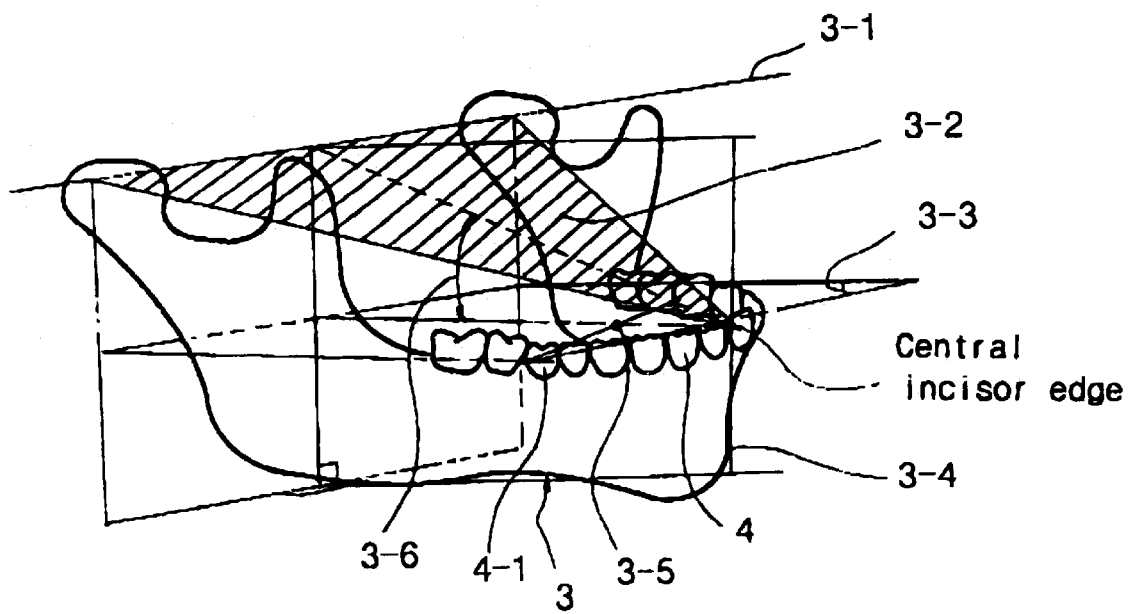
FIG. 2a is a schematic perspective view illustrating a general mandible.
Figure 2B:
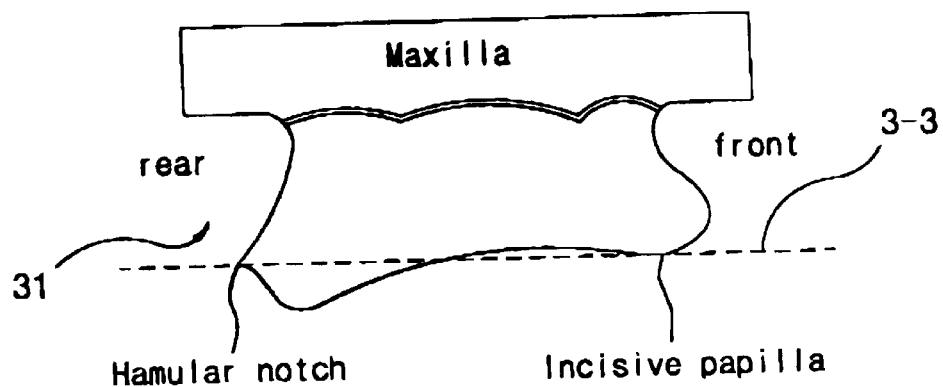
FIG. 2b is a schematic side view illustrating a general maxilla.
Figure 2C:
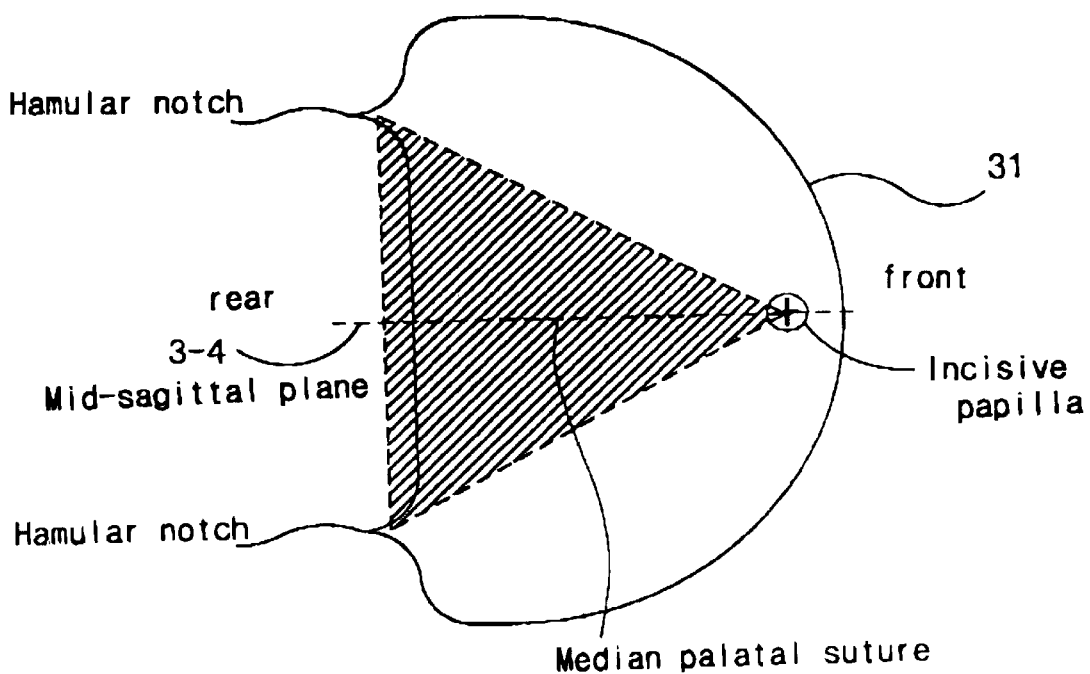
FIG. 2c is a schematic bottom view of the maxilla shown in FIG. 2b.
Figure 2D:
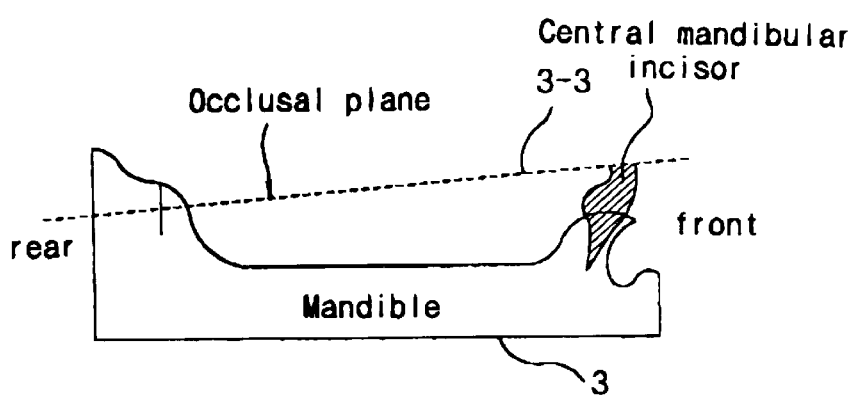
FIG. 2d is a schematic side view illustrating an edentulous mandible.
Figure 2E:
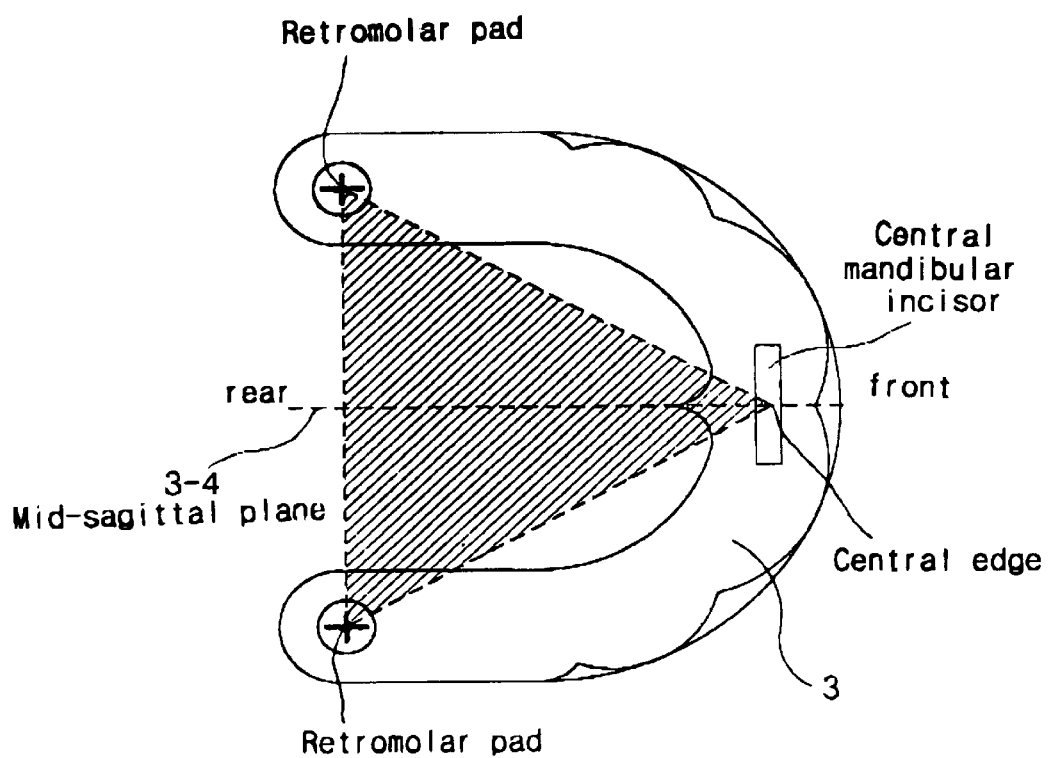
FIG. 2e is a schematic bottom view of the mandible shown in FIG. 2d.
Figure 3:
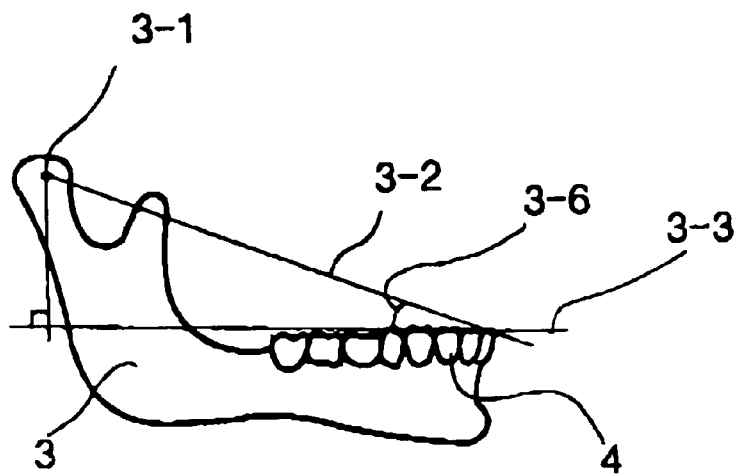
FIG. 3 is a schematic side view of a general mandible.
Figure 4:
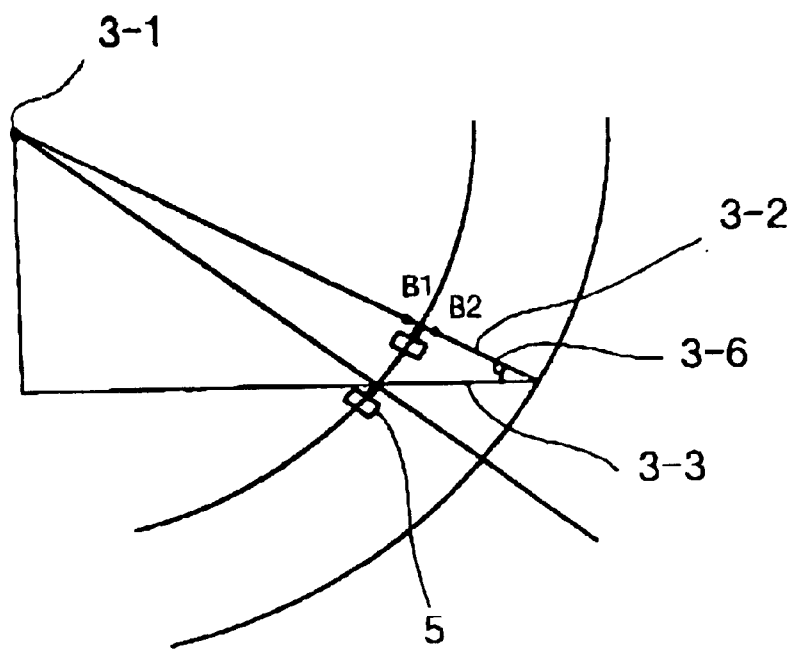
FIG. 4 is a schematic view illustrating a shift of a stylus on an occlusal plane of a general mandible.
Figure 5:
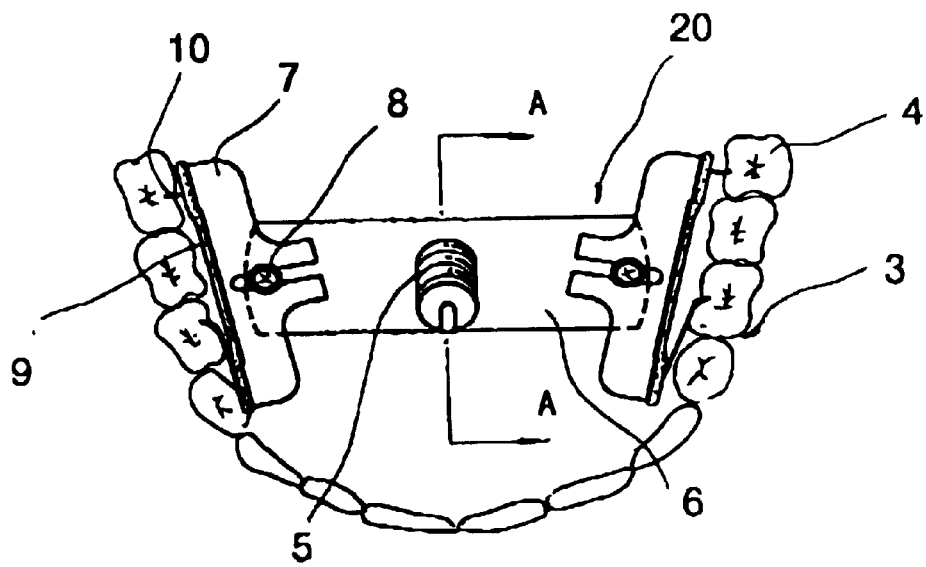
FIG. 5 is a plan view illustrating a conventional tracing device.
Figure 6:
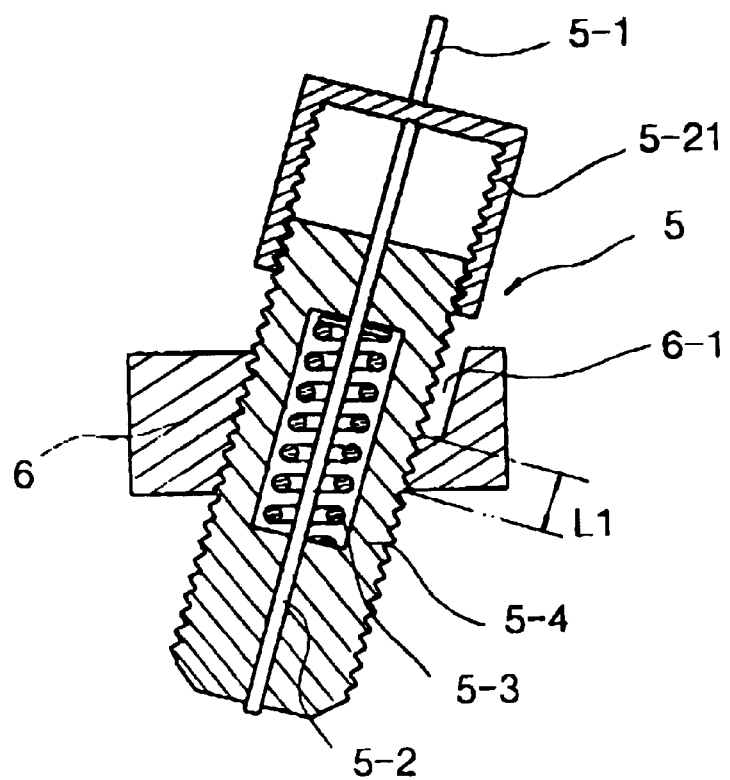
FIG. 6 is an enlarged cross-sectional view taken along the line A—A of FIG. 5.
Figure 7:
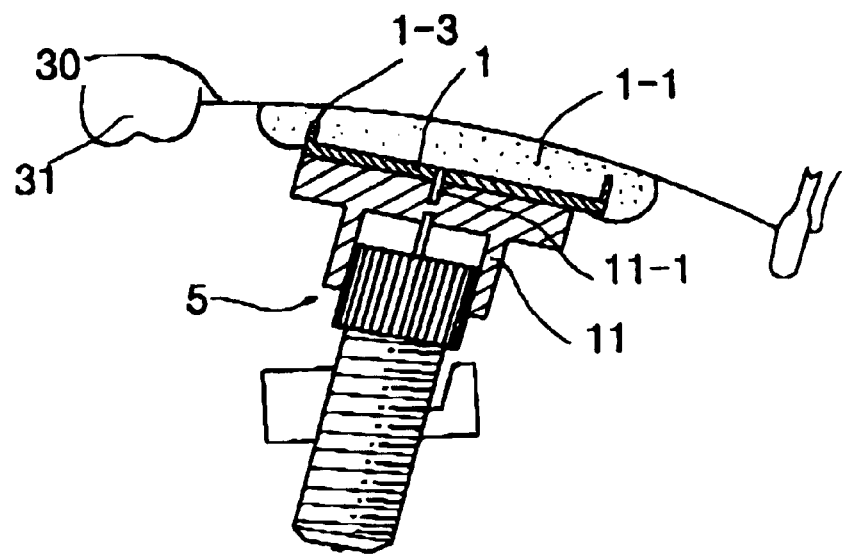
FIG. 7 is a cross-sectional view illustrating a state in which a tracing plate is mounted to a maxilla by use of the stylus shown in FIG. 6.
Figure 8:
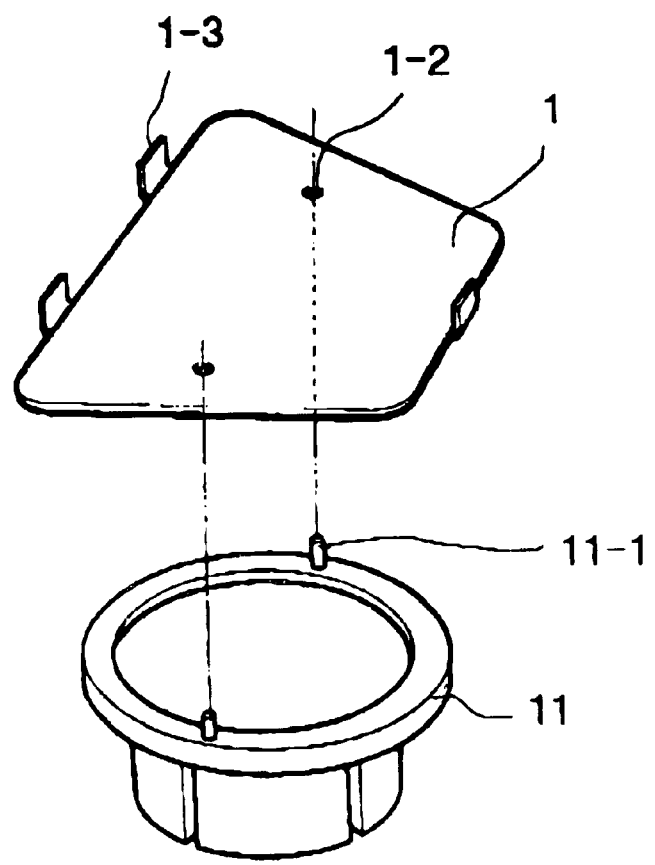
FIG. 8 is an exploded perspective view illustrating a cap temporarily supported by the conventional stylus and the tracing plate temporarily coupled to the cap.
Figure 13C:
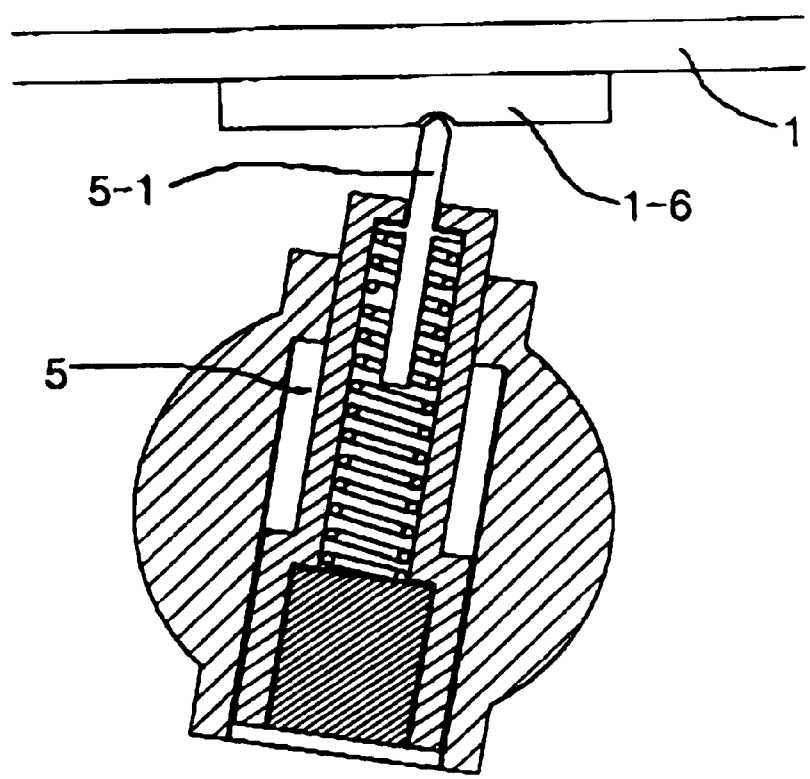

Now, the operation of the tracing apparatus according to the present invention will be described. A dental pattern of a patient is first copied. Dental casts (namely, maxillary and mandibular dental models) are then formed based on the copied dental pattern. The maxillary and mandibular dental models are subsequently mounted to an articulator. For a fully edentulous patient, the mounting of the dental models is carried out based on a maxillary-mandibular jaw relation obtained in accordance with a closed mouth impression technique. For a dentulous patient, the mounting of the dental models is carried out based on a centric occlusion of the patient. The tracing apparatus 100 of the present invention is then mounted to the mandibular dental model in the articulator. The mounting of the tracing apparatus 100 can be initially set in a convenient manner using the mounting reference die 90 shown in FIG. 12*a* or 12*b*. For an edentulous patient, the stylus 5 is erected in a state approximately perpendicular to the mandibular occlusal plane by use of the mounting reference die 90. In this state, the stylus 5 can be easily set so that it is positioned at a desired position. For a dentulous patient, the stylus 5 is oriented using the mounting reference die 90 so that it is forwardly inclined by an angle of about 17° with respect to the mandibular occlusal plane. In this state, lateral balancing of the tracing plate is conducted. In this case, the front and rear depth measuring bars 95 and 96 define a longitudinal reference line whereas the left and right lateral depth measuring bars 92-1 define a lateral horizontal relation with respect to the maxilla. Based on the defined longitudinal reference line and maxillary lateral horizontal relation, accordingly, the tracing plate can be laterally balanced with respect to the maxilla when it is mounted to the maxilla, as shown in FIGS. 12*b* and 12*c*. Thus, it is possible to previously diagnose a mismatching of the tracing plate with the maxillary dentition. By virtue of such a previous diagnosis, the tracing apparatus of the present invention can be conveniently applied to orthodontia, dental prosthesis, or dental remedy for dentulous patients. Even for dental prosthesis, a reference position can be easily and rapidly determined by virtue of the lateral horizontal lines 92, the line 94 orthogonal to the lateral horizontal lines 92, and the parabolic horizontal lines 93. For example, where it is necessary to form prosthesis or artificial dentures, the tracing apparatus 100 is mounted in an articulator, as shown in FIG. 9*a* or 9*b*, in order to measure the patient's centric relation as mentioned above. That is, the base plate 60 is mounted at a desired position by adjusting the support members 70 in accordance with the dentition of the patient. Thereafter, the initial position of the tracing apparatus 100 on the mandibular model in the articulator is set using the mounting reference die 90. The stylus 5 is then fixed in a desired orientation by the screws 54. For fully edentulous patients, the stylus 5 is fixed in such a fashion that it is forwardly inclined by an angle of about 17° with respect to a line perpendicular to the mandibular occlusal plane. Under this condition, the cap 11, which serves as a transfer plate, is fitted on the tip portion 5-1 of the stylus 5, as shown in FIG. 10*a*. In this state, a gel type binding material 1-1 is applied to a palatal surface portion of the articulator facing the cap 11. The maxilla of the articulator is then depressed in such a fashion that the tracing plate 1 is settled in the binding material 1-1, as shown in FIG. 7. In this state, the articulator is kept for several minutes until the binding material 1-1 is set. As a result, the tracing plate 1 is temporarily fixed to the maxilla. After the setting of the binding material 1-1, the maxilla 31 of the articulator is separated from the mandible 3 (not shown in FIG. 7). As a result, the stylus 5 and cap 11 are separated from the tracing plate 1. Of course, the tracing plate 1 is maintained in a state attached to the maxilla 31. Thereafter, the cap 11 is separated from the stylus 5. In this state, the arrangement of the tracing plate 1 is adjusted again with respect to the maxilla. Thereafter, the re-adjusted tracing plate 1 is fixed using a gel type binding material so that it is integral with the maxilla. The cap 11 is then fitted again on the tip portion 5-1 in such a fashion that the stylus 5 is perpendicular to the tracing plate 1. In this state, the screws 54 are unfastened, and the cap 11 is then adjusted to come into surface contact with the tracing plate 1. Then, the screws 54 are fastened. Preferably, the tracing plate 1 is provided at the front and rear ends thereof with coupling protrusions 1-4. By virtue of these coupling protrusions 1-4, it is possible to increase the coupling force of the tracing plate 1 and to achieve an easy transfer of the tracing plate to the maxilla. Next, the tracing device 100 of FIG. 9*a* or 9*b* and the tracing plate 1, to which the set binding material 1-1 is integrally coupled, are completely separated from the articulator. The separated tracing apparatus 90 and tracing plate 1 are then mounted to the dentition of the patient, as shown in FIG. 9*a* or 9*b*. Since the dental model mounted to the articulator has the same shape as the dentition of the patient, only one of them is illustrated in FIG. 9*a* and 9*b* without any distinction therebetween. Where there is a tolerance between the dental model of the articulator and the dentition of the patient, this can be compensated for by adjusting the screws. For an easy and convenient adjustment, the screws 54 may be coupled in opposite directions in such a fashion that their heads are opposite to each other. In this case, the adjustment can be conveniently achieved by adjusting only one of the screws, in particular, the screw, the head of which faces upwardly. For dentulous patients, the tracing of a Gothic arch is carried out under the condition in which the height of the stylus 5 is varied in a range of 3 to 4 mm by fastening or unfastening the threaded portion 5-5 of the stylus 5. Thereafter, the forward inclination of the stylus 5 corresponding to an angle of 17° is adjusted again so as to align the tip of the stylus with the apex of the traced Gothic arch. This adjustment of the stylus can be achieved by unfastening the screws 54 to allow a pivotal movement of the ball 40, thereby finely adjusting the orientation of the ball 40, and then fastening the screws 54 to set the ball 40 with the finely adjusted orientation. The setting of the ball 40 is possible by virtue of the circular holes 53 of the support plate 50 and base plate 60. That is, the arc-shaped surfaces of the circular holes 53 come into surface contact with the surface of the ball 40 under pressure as the support plate 50 and base plate 60 are clamped to each other when the screws 54 are fastened. The reason why the height of the stylus 5 is adjusted by fastening or unfastening the threaded portion 5-5 of the stylus 5 is because for dentulous patients other than edentulous patient, the stylus 5 can move longitudinally and laterally along with the mandible without any phenomenon in which both the stylus 5 and the mandibular dentition do not come into contact with the maxillary dentition in so far as the tip of the tip portion 5-1 is positioned at a level higher than the occlusal plane 3-3 shown in FIG. 2a. Under this condition, when the mandible of the patient moves longitudinally and laterally, the stylus 5 of the tracing apparatus 100 traces a Gothic arch, thereby recording a Gothic arch trace including an apex 2, a forward longitudinal mandibular movement path 2-1 and opposite lateral mandibular movement paths 2-2 on the tracing plate 1, as shown in FIG. 1. The tracing plate 1 recorded with the Gothic arch trace is then separated from the oral cavity of the patient, together with the set coupling material 1-1. A separate disc, which has an aperture corresponding to the apex 2 of the Gothic arch trace, is subsequently attached to the tracing plate 1 in such a fashion that its aperture is vertically aligned with the apex 2 of the Gothic arch trace. Under this condition, the disc is fixed to the tracing plate 1 by applying a wax material therebetween and then setting the wax material. Thereafter, the tracing plate 1 attached with the disc and the tracing apparatus 100 are mounted again in the oral cavity of the patient. The patient then closes the oral cavity under the condition in which the tip portion 5-1 of the stylus 5 is fitted in the aperture of the disc. In this state, a bite material is put on desired portions of the maxilla and mandible between the tracing device 20 and tracing plate 1. After the bite material is set, a maxillary-mandibular jaw relation of the patient is obtained. Subsequently, the tracing apparatus 100, the tracing plate 1, and the set bite material with a recording are separated from the oral cavity of the patient, and then mounted again to the maxillary and mandibular dental models of the articulator while keeping an occlusal relation corresponding to the recording. Using the articulator with such an occlusal relation, dental diagnosis and remedy for the patient may be conducted. On the other hand, it may be necessary to directly correct the occlusal relation in the oral cavity for patients requiring an orthodontia of dental prosthesis or an occlusal adjustment of the overall dentition, patients set with erroneous artificial dentures, or sprint-set patients having disturbances of the temporomandibular joint. For such patients, a centric relation is traced using the stylus of FIG. 5 which is of a fixed type. This stylus is then replaced by the stylus of FIG. 13a which is of a slidable type. The stylus of FIG. 13a is used in the oral cavity, as shown in FIG. 13c. That is, when the patient closes the oral cavity, the tip member 5-1 of the stylus is downwardly depressed by the tracing plate 1, so that it moves downwardly against the spring force of the compression coil spring 5-13 arranged in the inner space 5-6 of the rod portion 5-4. Where the patient has a tooth of an abnormally large length, the downward movement of the tip member 5-1 is incompletely carried out. Such a phenomenon is immediately checked by the doctor. In this case, an occlusal adjustment may be conducted using a desired process such as grinding. Thus, dental prosthesis may be conducted after eliminating an abnormality in the centric relation of the mandible as mentioned above.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

As apparent from the above description, the present invention provides a tracing apparatus including a stylus threadedly coupled to a selectively pivotable ball in such a fashion that it pivots in vertical, longitudinal, and lateral directions, thereby being capable of conveniently adjusting its position and orientation so that it is set to conform to a hinge movement of a patient. The ball serves as a coupling nut for the stylus and has a cylindrical stylus guide portion adapted to reduce an instability of the stylus during a tracing operation thereof. In particular, both the stylus and ball are fixed by a base plate and a support plate which occupy a reduced height. Accordingly, it is possible to easily mount the tracing apparatus in the patient's oral cavity. Furthermore, there is an effect of achieving a direct occlusal adjustment in the patient's oral cavity by replacing the fixed type stylus (FIG. 5) by the slidable stylus (FIG. 13a).

In addition, it is possible to correct any mismatching between the maxilla and the dental occlusal plane using a mounting reference die in accordance with the present invention. The mounting reference die also serves as a guide plate for maintaining an accurate parallel relation of a tracing plate with respect to the maxilla when the tracing plate is mounted to the maxilla.

What it is claimed is:

1. An apparatus for tracing a centric relation of a mandible comprising a stylus arranged at a point, where an occlusal plane and a mid-sagittal plane cross a line extending between central fossae of mandibular first molars, and a tracing plate adapted to be mounted to a maxilla at a region corresponding to the stylus, further comprising:

a ball threadedly coupled to said stylus in such a fashion that it is fitted around said stylus in the form of a nut and cylinder;

a base plate having a circular hole provided with an arc-shaped surface serving as a seat for said ball;

a support plate arranged over said base plate and coupled to said base plate while being vertically spaced from said base plate, said support plate having a circular hole provided with an arc-shaped surface cooperating with said arc-shaped surface of said base plate to clamp said ball therebetween when said support plate is in a state coupled to said base plate; and a plurality of support members each mounted to a desired portion of said base plate at one end thereof and engaged with a desired surface portion of a dentition at the other end thereof, thereby maintaining said base plate at a desired position.

2. The apparatus in accordance with claim 1, wherein said ball comprises:

a ball body;

a cylindrical recess vertically formed through said ball body and adapted to receive said stylus, said cylindrical recess being provided at a lower end thereof with a larger-diameter opening for allowing said stylus to be inserted into said cylindrical recess and at an upper end thereof with a smaller-diameter opening for allowing said stylus to extend upwardly from said ball;

a pair of tubular skirts extending from upper and lower ends of said ball body, respectively; and threads formed on a side surface of said cylindrical recess at a lower portion of said cylindrical recess.

3. The apparatus in accordance with claim 2, wherein said stylus comprises:

a vertically-extending rod portion received in said cylindrical recess while being partially upwardly protruded through said smaller-diameter opening of said cylindrical recess;

a threaded portion extending downwardly from a lower end of said rod portion, said threaded portion being threadedly coupled to said threads in said cylindrical recess; and a tip portion extending upwardly from an upper end of said rod portion.

4. The apparatus in accordance with claim 2, wherein said stylus comprises:

a vertically-extending tip member having a stopper at a desired length portion thereof, said tip member also having a downward extension at a lower end thereof;

a hollow rod portion for receiving said tip member in such a fashion that it allows said tip member to be upwardly protruded therefrom and cooperates with said stopper to limit said upward protrusion of said tip member;

a hollow threaded portion extending downwardly from a lower end of said rod portion in such a fashion that it is integral with said rod portion, said threaded portion having outer and inner threads and being threadedly coupled to said ball;

a plug member threadedly coupled to said threaded portion in such a fashion that it is fitted in said threaded portion; and a compression coil spring arranged between said stopper and said plug member in the interior of said rod member, said compression coil spring serving to always urge said tip member in an upward direction.

5. The apparatus in accordance with claim 1, wherein said stylus comprises:

a vertically-extending tip member having a stopper at a desired length portion thereof, said tip member also having a downward extension at a lower end thereof;

a hollow rod portion for receiving said tip member in such a fashion that it allows said tip member to be upwardly protruded therefrom and cooperates with said stopper to limit said upward protrusion of said tip member;

a hollow threaded portion extending downwardly from a lower end of said rod portion in such a fashion that it is integral with said rod portion, said threaded portion having outer and inner threads and being threadedly coupled to said ball;

a plug member threadedly coupled to said threaded portion in such a fashion that it is fitted in said threaded portion; and a compression coil spring arranged between said stopper and said plug member in the interior of said rod member, said compression coil spring serving to always urge said tip member in an upward direction.

6. A mounting reference die for a tracing plate included in a Gothic arch tracing apparatus comprising:

a die plate;

a pin hole formed through said die plate and adapted to receive a tip of a stylus included in said tracing apparatus;

a plurality of longitudinally spaced lateral horizontal lines formed on an upper surface of said die plate and adapted to measure a lateral inclination of said tracing plate with respect to an occlusal plane;

a plurality of parabolic horizontal lines formed on said upper surface of said die plate to have parabolic shapes of different sizes conforming to those of different patients' dentitions defined on said occlusal plane, respectively, each of said parabolic horizontal lines being laterally symmetric with respect to the center thereof;

a front depth measuring bar downwardly protruded from a lower surface of said die plate and arranged at a front portion of said die plate on a center line extending through the centers of said lateral horizontal lines while being orthogonal to said lateral horizontal lines;

a rear depth measuring bar serving as a vertical adjustment bar and being upwardly protruded from said upper surface of said die plate in rear of said front depth measuring bar, said rear depth measuring bar serving to measure a depth of a maxilla in cooperation with said front depth measuring bar;

a plurality of lateral depth measuring holes formed through said die plate at opposite ends of said parabolic horizontal lines in such a fashion that they are laterally symmetric with respect to said center line;

a pair of lateral depth measuring bars fitted in two laterally symmetric ones of said lateral depth measuring holes selected in accordance with the size of said maxilla, said lateral depth measuring bars serving to measure a depth of said maxilla at opposite lateral ends of said oral cavity, respectively;

a bolt hole formed through a central portion of said die plate; and a guide bolt vertically inserted into said bolt hole and adapted to establish an accurate lateral horizontal relation of said tracing plate with respect to said maxilla, said guide bolt including a clamp bolt inserted into said bolt hole, a pair of clamp nuts threadedly coupled to said clamp bolt at opposite sides of said die plate, respectively, to clamp said die plate in a state perpendicular to said clamp bolt, and a horizontal guide surface formed at a head portion of said clamp bolt and adapted to maintain said tracing plate in parallel to said die plate.

* * * * *